United States Patent [19]

Horstman et al.

[11] Patent Number: 5,006,474
[45] Date of Patent: Apr. 9, 1991

[54] BI-DIRECTIONAL LATERAL CHROMATOGRAPHIC TEST DEVICE

[75] Inventors: Frederick C. Horstman, Laguna Niguel; Julie Whiteside, Orange, both of Calif.

[73] Assignee: Disease Detection International Inc., Irvine, Calif.

[21] Appl. No.: 133,804

[22] Filed: Dec. 16, 1987

[51] Int. Cl.⁵ .................. G01N 33/543; C12Q 1/24
[52] U.S. Cl. .................. 436/524; 436/170; 436/528; 436/807; 436/808; 436/809; 436/825; 435/7.93; 435/287; 435/7.94; 422/61; 422/56; 422/57; 422/58
[58] Field of Search .............. 436/514, 524, 527, 170, 436/528, 539, 807, 808, 809, 825, 824, 161, 162, 515, 810; 422/61, 56, 57, 58, 60, 69, 70

[56] References Cited

U.S. PATENT DOCUMENTS

| 3,420,205 | 1/1969 | Morison | 422/56 |
| 4,235,601 | 11/1980 | Deutsch et al. | 436/514 |
| 4,435,504 | 3/1984 | Zuk et al. | 435/7 |
| 4,678,757 | 7/1987 | Rapkin et al. | 436/169 |
| 4,761,381 | 8/1988 | Blatt et al. | 436/165 |
| 4,822,565 | 4/1989 | Kohler | 436/810 X |
| 4,857,453 | 8/1989 | Ullman et al. | 435/7 |
| 4,883,765 | 11/1989 | Kloepfer | 436/63 |
| 4,900,663 | 2/1990 | Wie et al. | 435/7 |
| 4,918,025 | 4/1990 | Grenner | 436/165 |

Primary Examiner—David L. Lacey
Assistant Examiner—Janelle D. Waack
Attorney, Agent, or Firm—Knobbe, Martens, Olson & Bear

[57] ABSTRACT

A chromatic test device for the performance of immuno- or chemical assays wherein a unitary planar fibrous filter body incorporates a sample application zone, a separation zone and a reaction zone and the application zone is in fluid communication with a first absorbent and the reaction zone is in fluid communication with a second absorbent to establish bilateral flow of the fluid component of the sample and of the analyte applied to the zones during the performance of an assay.

27 Claims, 2 Drawing Sheets

BI-DIRECTIONAL LATERAL CHROMATOGRAPHIC TEST DEVICE

BACKGROUND OF THE INVENTION

The invention relates to a diagnostic device for performing solid phase immunoassays to detect the presence of antigens or antibodies in biological or non-biological fluids. The teachings of the invention are incorporated in a bi-directional lateral chromatographic device for use in solid phase immunoassays or for the non-immunological detection or quantitation of proteins or substances in biological or non-biological fluids.

More particularly, the invention relates to devices and methods which utilize filter means for testing biological fluids to detect the presence of analytes such as bacterial, viral, parasitic, or fungal antigens and immunoglobulins, hormones, serum proteins, drugs and the like.

Typical of prior art devices presently in use are the teachings of U.S. Pat. No. 4,623,461, which discloses a filter body located in a housing having an opening therein for the reception of a suspension sample to permit the upper face of the filter to trap colored or particulate matter contained within the specimen and prevent such matter from reaching the bottom face of the reaction zone, which has been previously treated with a suitable reactant. The perimeter of the filter is engaged with a suitable absorbent body and the absorbent body is intended to receive the outward diffusion of liquids applied to the filter.

One of the disadvantages of the '461 construction lies in the fact that the fluid flow from the point of application of the suspension to the absorbent body is unidirectional and a subtantial accumulation of solids at the point of application of the sample suspension is inevitable, which will seriously impinge upon the resultant chromatological or other type of test reading imparted by the device.

U.S. Pat. No. 3,825,410 discloses a disposable combined storage and reaction cell for use in the performance of chemical and biological reactions which receives reactants dispensed therein and maintains the same in stored condition so that they remain stable. Reactants will not mutually react until such time as it is required to initiate the reaction.

The immobilization of the reactants is accomplished by such procedures as freeze drying and the reaction is initiated by the introduction of a sample to be analyzed, whereafter separation of bound and free ligand can be performed either within the unit itself or externally.

The reaction cell of the '410 patent may include a filter so that the entire process of separation can be completed within the reaction cell and the filter be removed from the reaction cell and submitted for radioactivity or other tracer counts.

U.S. Pat. No. 3,888,629 discloses a reaction cell for performing various types of assays which incorporates a matrix pad of absorbent material retaining the necessary reagents for the reaction and serving as a site in which the reaction totally occurs. A separable lower chamber incorporates absorbent material abutting the matrix pad to promote filtration through the pad after the reaction has taken place.

Both patents are characterized by the mere utilization of the filter as a pass-through device which is time-consuming and which is hindered by the deposition of solids out of the suspension sample.

OBJECTS AND ADVANTAGES OF THE INVENTION

One of the objects of the invention is the provision of a diagnostic device which incorporates a planar filter body having sample application, separation and reaction zones, said filter body being configured in such a manner that the bulk of the solids in the suspension sample are retained in the sample application zone and the fluid is caused to migrate bilaterally through the interstices of the filter by the fluid communication of absorbent means with the application and reaction zones.

Consequently, the unilateral directional flow which causes accumulation of solids in the reaction zone in the previously discussed prior art devices is eliminated in the test device of our construction because the rapid bilateral flow achieved by the construction of the device causes immediate deposition of solids out of the fluid component of the suspension.

Another object of the invention is the provision of a diagnostic test device of the aforementioned character wherein the planar filter incorporates a sample application zone which is relatively large and which is connected to the reaction zone by a separation zone, the length of the separation zone being proportioned to the character of the suspension sample applied to the application zone, and the separation and application zones cooperate to retain the bulk of the solids or particulate matter in the application and separating zones so that the immuno-reagent or chemical test reagent deposited in the reaction zone, when subjected to the test procedures and analytes, will have a minimum of or no particulates embodied therein which would cause the emission of high background signals, thus creating a negative effect on the test readout.

Another important object of the invention is the provision of a composite housing filter conjugate which is characterized by ease of assembly and application. The test device of the invention is designed particularly for use in the field for the testing of various human and animal diseases or for various chemical tests involving the utilization of blood samples from humans and animals, and it is capable of giving test results equal to laboratory results within a matter of minutes depending upon the sample solution which is applied to the specific device.

Another object of the invention is the provision of a method of performing a test by the utilization of the device of the invention which incorporates a plurality of simple steps which can be carried forth by non-laboratory personnel in the field and which can provide such personnel with an almost immediate readout of the presence or absence of the sought-after infection or drug, or the like.

BRIEF DESCRIPTION OF THE DRAWINGS

Other objects and advantages of the invention will be apparent from the following specification and the accompanying drawings, which are for the purpose of illustration only, and in which.

DESCRIPTION OF THE PREFERRED EMBODIMENTS OF THE INVENTION

The chromatic assay device of the present invention may be used to perform solid phase immunoassays for the detection of antigens or antibodies, hereinafter referred to as analytes, in biological and non-biological fluids. The device may be non-immunologically used to identify and/or quantitate proteins or substances in biological and non-biological fluids. The device may be utilized to perform assays such as competitive or non-competitive enzyme-linked immunoassays, enzyme-multiplied immunoassays, enzyme-inhibition assays, heterogeneous or homogeneous fluorescent immunoassays, chemiluminescent and bioluminescent assays, these assays utilizing various labelled probes, and the like.

Obviously, the particular analyte test to be used will depend upon the chosen sample and the desired result to be achieved.

Figure 1:
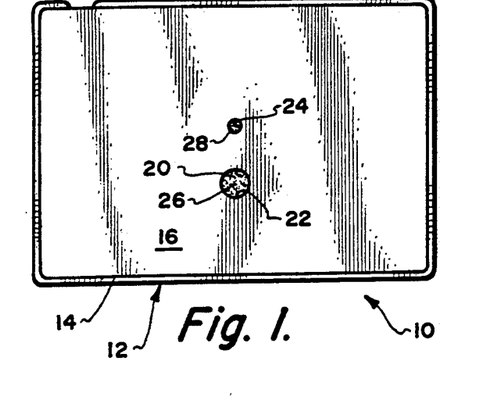
FIG. 1 is a top plan view of a typical device of the invention.

Referring to the drawings, and particularly to FIG. 1 thereof, we show a test device 10 constructed in accordance with the teachings of our invention which is incorporated in a housing 12, said housing consisting of a lower or bottom component 14 and a cover or closure 16. The bottom component 14 of the housing may be fabricated by injection molding from suitable synthetic plastic materials such as polyethylene and, as will appear further hereinbelow, is specifically designed to receive a flat co-planar filter 20.

The closure 16 overlies the filter 20 and is secured to the housing by pressure-sensitive adhesive or other adhering means and incorporates an application port or opening 22 and a reaction port or opening 24, said ports communicating, respectively, with the application zone 26 and the reaction zone 28 of the filter.

Figure 2:
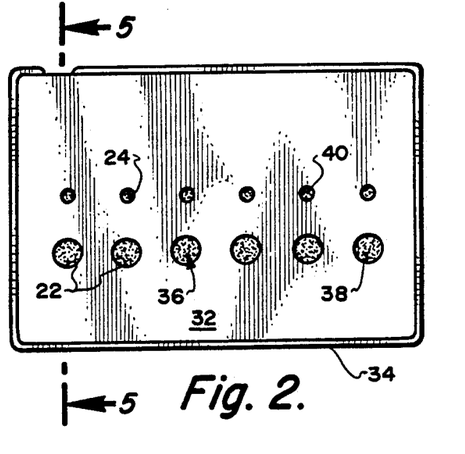
FIG. 2 is a device similar to FIG. 1 with the exception that it incorporates a plurality of application and reaction zones.

The test device 10 is designed for the performance of a single test, but, as best shown in FIG. 2 of the drawings, a device 30 incorporating a multiplicity of application ports 22 and reaction ports 24 can be provided in a closure or cover 32 which overlies a suitably configured, as will be explained in greater detail below, lower housing portion 34 and filter 36. The ports 22 and 24 respectively overlie application and reaction zones 38 and 40 of the filter 36.

The filters 20 and 36 are constituted by a planar glass fiber matrix which is sandwiched between the lower component of the housing and the cover therefor.

Figure 3:
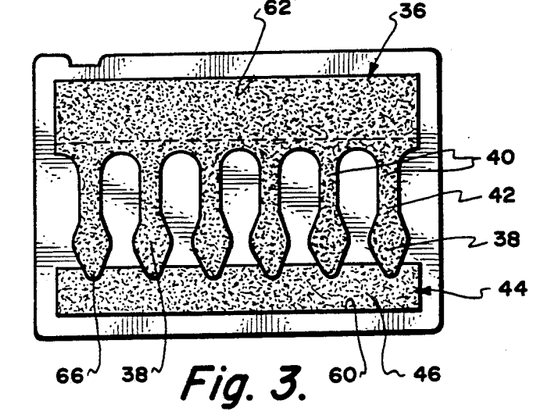
FIG. 3 is a top plan view showing the housing of the device of FIG. 2 with the cover removed therefrom to illustrate the location of and configuration of the filter and the relation thereof with the absorbent means and the particular design of the housing to encapsulate the filter and absorbent means.

As best shown in FIG. 3 of the drawings, the filter 36 includes a plurality of application zones 38 and reaction zones 40 which are maintained in fluid communication by separation zones 42. The separation zones 42 are of elongate configuration and establish fluid communication between the application zones 38 and the reaction zones 40.

The application zones 38 are shown as being roughly bulbous or trapezoidal in configuration and provide a relatively large area for the application of the test sample. For a purpose which will be explained hereinbelow, the separation zones 42 are of relatively restricted width in comparison with the width of the application zones 38.

Located in fluid communication with the application zones 38 is first absorbent means 44 constituted by an elongated strip 46 of absorbent material. Similarly, a second absorbent means 48 constituted by an elongated strip 52 is disposed in fluid communication with the multiplicity of reaction zones 40 provided by the filter 36.

Figure 4:
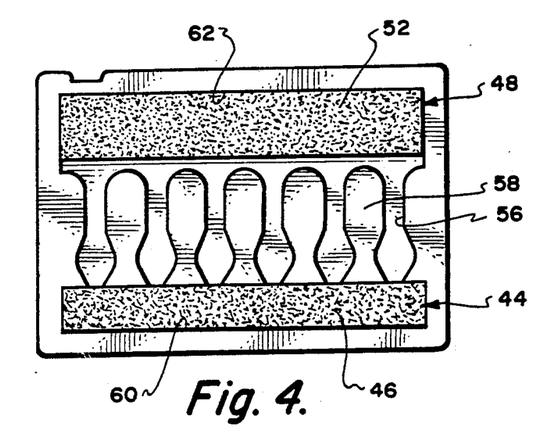
FIG. 4 is a view similar to FIG. 3 illustrating removal of the filter to disclose the relationship of the absorbent means with the housing and the particular configuration thereof.
Figure 5:
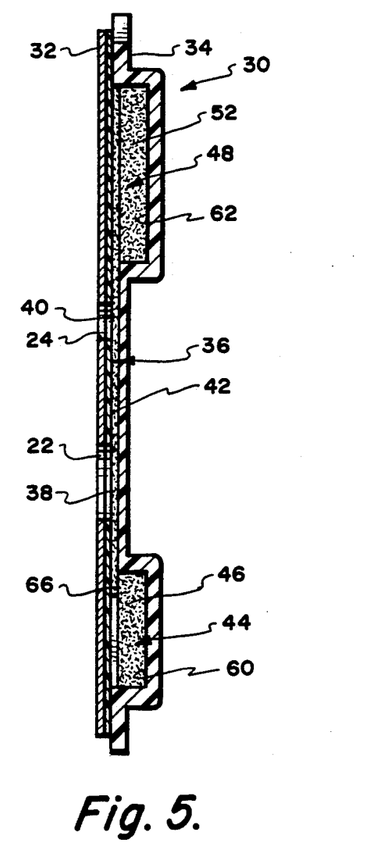
FIG. 5 is a vertical sectional view taken on the broken line 5—5 of FIG. 2 and illustrates the fluid relationship of the filter with the absorbent means and the filter and absorbent components with the specific design of the housing and cover therefor.
Figure 6:
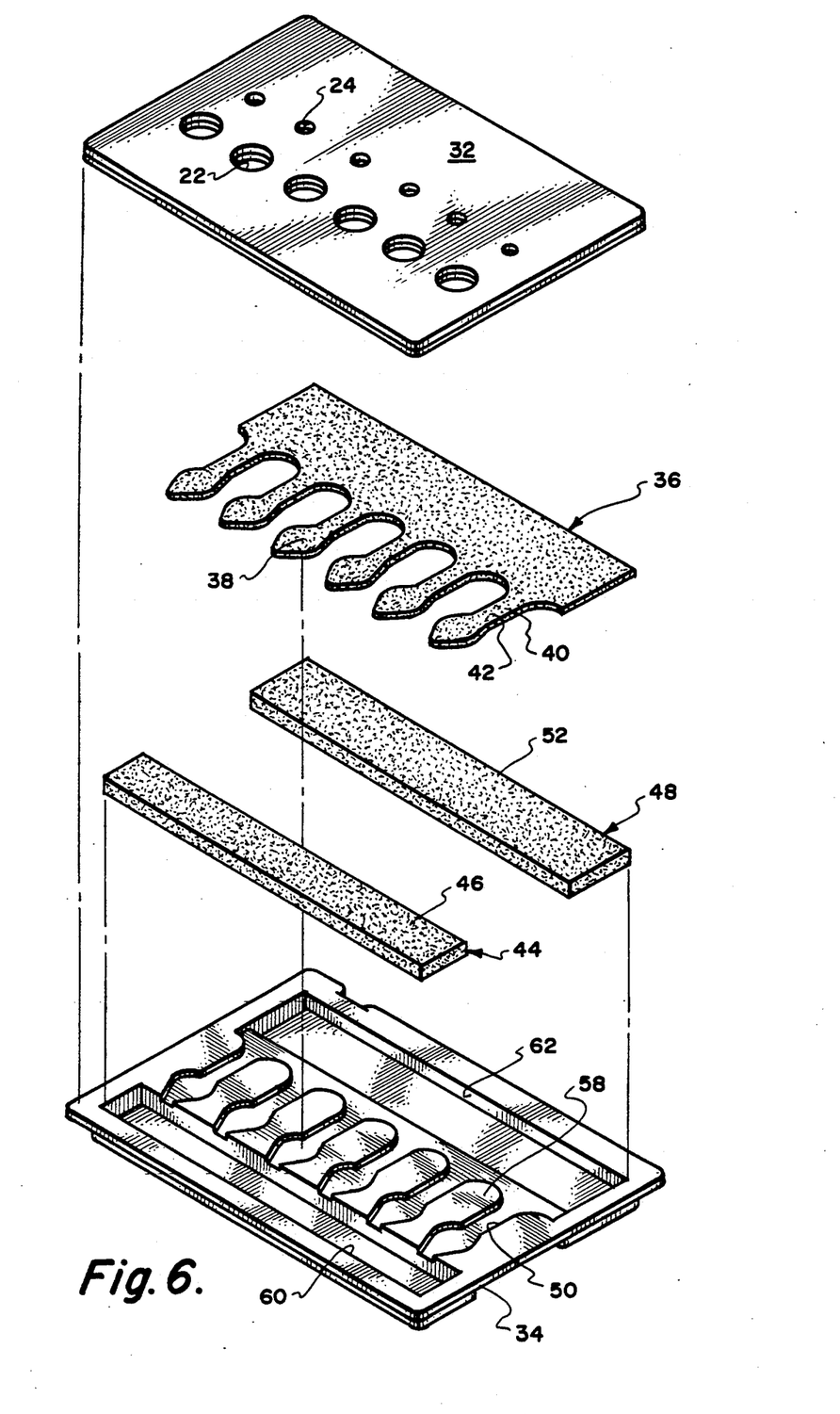
FIG. 6 is an exploded view illustrating the various components of the test device.

The lower or bottom portion 34 of the housing of the test device 30 is configured, as best shown in FIGS. 4 and 5 of the drawings, to provide receptacles 56 for the application, separation and reaction zones of the filter 36 so that fluid flow is confined in the plane of the filter 36 because of the sandwich created between the closure 32 and the lower portion 34 of the housing. The receptacles are defined by integrally molded lobes 58 in the body of the lower portion 34 of the housing and stringently confine the relevant portions of the filter in the receptacles 56.

Juxtaposed to the receptacles 56 is a first elongated rectangular well 60 for the reception of the first absorbent means 44, and a corresponding well 62 is provided for the reception of the second absorbent means 48.

The closure or cover 32 of the device 30 can be fabricated from vinyl or other plastic sheet material and may be adhesively or otherwise secured to the bottom portion 34 of the housing of the test device 30.

The application, separation and reaction zones are contiguous within the co-planar surfaces of the glass fiber matrix. A sample or samples applied to the sample application zones 38 will migrate laterally by capillary and chromatographic action. As will be described hereinbelow in greater detail, the fundamental result achieved by the test devices constructed in accordance with the teachings of the invention is bilateral flow of the fluid component of suspensions applied to the application zones 38.

During the bilateral migration, particulate matter present within the sample volume, i.e., cellular components of whole blood, salt crystals of urine or protein aggregates of serum or plasma, etc., are filtered from the fluid portion of the applied sample by particle size exclusion dictated by the mean pore size of the glass fiber matrix. Since the mean pore size of the glass fiber matrix is not an absolute value, but, rather, represents a Poisson distribution of a range of pore sizes, the length and width of the separation zone will be influenced and dictated by the mean porosity of the glass fiber matrix. Likewise, since the mean diameter of particulates within the sample will vary, a separation gradient will be realized within the body of the separation zone, with larger particulates remaining closer to the application zone, while smaller particulates will migrate some distance from the application zone.

Therefore, the length and width of the separation zone between the reaction and sample application zones must be carefully established empirically in order to position the reaction zone at a proper distance from the sample application zone to prohibit an inhibitory quantum of particulates from entering the reaction zone. If the separation zone length is too short, some particulates may enter the reaction zone; if too long, the volume of filtered sample fluid containing the desired analyte to be detected may be insufficient for optimal detection.

Bilateral migration of the fluid portion of the applied sample is also channeled in a direction 180 degrees away from the separation zone and, subsequently, the reaction zone, by the tapered constriction in the lateral boundaries of the trapezoidal glass fiber matrix. This constriction of the glass fiber matrix favors migration of the sample through the separation zone in the direction of the reaction zone, yet still allows for some migration of fluid away from the separation and reaction zones, facilitating removal of unwanted or interfering debris (particulates, protein aggregates, unreacted test reagents) from the reaction zone upon subsequent application of wash solution and/or test reagents to the reaction zone. In essence, this design functions as a safety valve and reduces or eliminates back-washing of unreacted components into the reaction zone which may cause high background signals.

Sandwich relationship between the filter 36 and the cover 32 with the bottom portion 34 of the housing of the filter and with the associated absorbent means 44 and 48 is illustrated in the cross-sectional view of FIG. 5, which, of course, is equally applicable to the test device of FIG. 1, as well as the test device of FIG. 2. It will be noted from the showings of FIGS. 3 and 5 that a portion of each application zone 38 is in fluid communication with the corresponding first absorbent means 44, as best shown at 66 in FIGS. 3 and 5 of the drawings. Consequently, the absorbent means 44 is in fluid communication with the application zones 38 and causes a bilateral flow of fluid from the sample being applied to the application zones simultaneously with flow in the opposite direction from the application zones 38 into the separation zones 42.

The bilateral flow through the separation zones 42 is facilitated by the location of the reaction zones 40 adjacent to a relatively large area of the filter 36, shown, in the particular embodiment of the test device, as generally rectangular in configuration and overlying the second absorbent means 48.

Consequently, bilateral flow established in this manner reduces the hydraulic pressure in the application zones 38 and causes rapid settling of particulates or other inclusions in the sample suspension, thus causing rapid settling out of the particulates or other detritus before reaching the reaction zones 40.

It will also be noted that the second absorbent means 48 is of much larger dimensions than the absorbent means 44, causing more rapid absorption of the excess fluid of the sample and causing the accentuation of the bilateral flow phenomenon achieved by the filter design and its association with the first and second absorbent means.

It will be readily apparent to those skilled in the art that the configuration of the application zones 38 can be readily altered to accommodate the needs of the particular samples being tested by the devices 10 and 30 and, furthermore, as specified hereinabove, the length and width of the separation zones be empirically established to conform to the bilateral flow patterns to be established for the particular sample.

Moreover, the relative dimensions and depth of the absorbent means 44 and 48 can be altered to establish greater or lesser fluid communication between the application zones 38 and reaction zones 40, respectively.

A typical glass fiber matrix filter has its source in Eaton-Dikeman Division of Filtration Sciences, Mount Holly Springs, Pennsylvania. The weight is 71 gm/m$^2$; the depth is 0.43 mm; the mean pore size is 0.6 micron (u); the mean fiber diameter is 0.7u (0.25u to 1.5u); and the composition is borosilicate glass.

The dimensions of the application zone are 8 mm in diameter, and the separation zone 4 mm × 9mm.

These dimensions are suitable to effect separation of cells, protein aggregates or other debris from a 30–40 ul sample of human whole blood or serum applied to the sample application zone followed by a wash volume of 50–60 ul applied to the same. Modification of the preferred embodiment is indicated if the whole blood sample is from an animal other than a human, such as equine or bovine whole blood, which generally has smaller red blood cell diameters (5.5u or 5.9u, respectively) than human (6.9u–8.1u). In this instance, a glass fiber matrix of a smaller pore size would be desirable, or, alternately, a longer or shorter separation zone may be required.

Although the filters 20 and 36 are described as fabricated in accordance with the previously set forth specifications, it will be obvious to those skilled in the art that the filter means can be made of any porous material capable of drawing liquid through its structure by capillary action. The pores of the filter matrix should, obviously, be sufficiently small to accomplish filter separation of the insolubilized components of the test sample from solubilized components.

The filter may be composed of such materials as glass fiber filter paper, nitrocellulose, plastic, synthetic polymer, cellulose, cellulose acetate, and various other equivalent materials having the qualities and characteristics described hereinabove.

Of course, it is desirable to utilize materials which are inert and chemically non-reactive with the analytes and washing solvents with which the test device is to be utilized.

The test devices 10 and 30, of course, have their respective reaction zones 28 and 40 treated with specific analyte reactants. Localized regions of the respective filters 20 and 36 are treated to provide the reaction zones 28 and 40 to prepare the test devices 10 and 30 for use with a predetermined test specimen without any preparatory additions to the test devices. For example, a binding protein could be placed in the reaction zones to which an antibody is bound, which antibody is immunologically reactive with a specific antigen.

Consequently, when a specimen is applied to the application zones 26 and 38 through the application ports 22, the fluid component of the suspension is immediately subjected to the bilateral action achieved by the specific construction of the test devices alluded to hereinabove.

The absorbent material utilized in the first and second absorbent means 44 and 48 may be of any suitable material, such as hydrophilic polymers, particulate absorbents, glass fiber, carbon fiber, cellulose fiber, wood pulp or sponge material.

As previously mentioned, the size and shape of the respective absorbent means 44 and 48 is dictated by the volumetric considerations applicable to the specific test for which the test devices 10 and 30 are designed, and corresponding diminishment or enhancement of the absorptive capacity of the first and second absorbent means 44 and 48 result from empirical calculations of the needs for the establishment of greater or lesser bilateral flow of the fluid components of the test specimen.

METHOD OF THE INVENTION

In practicing the method of the invention, a suitable volume of sample is applied directly to the sample application zone of the glass fiber matrix. A suitable volume of wash reagent is then applied to the same area of the sample application zone.

Capillary and chromatographic forces within the body of the glass fiber matrix draw the fluid portion of the sample primarily in the direction of the separation zone but, also, secondarily in the opposite direction. The bilateral flow is defined by the lateral boundaries of the glass fiber matrix and the fluid communication of the application and reaction zones with their respective absorbent means. As the fluid migrates through the separation zone, particles larger than the mean pore size of the glass fiber matrix are restricted in their lateral migration toward the reaction zone, so that only the fluid portion of the sample reaches and flows into and through the reaction zone. The analyte, contained within the fluid portion of the sample reacts and binds with the specific complimentary immuno-reagent (antigen or antibody) or chemical test reagents, which have been immobilized to the glass fiber matrix in the area of the reaction zone.

Subsequently, a suitable volume of wash reagent is applied directly to the reaction zone. This washes away unreacted sample components which may interfere with subsequent steps, in bilateral directions, again defined by the lateral boundaries of the glass fiber matrix, the directions being 1) away from the separation and sample application zones, and 2) toward the separation and sample application zones, reversing the original direction of flow.

Wash in the latter direction inhibits or prevents previously filtered particulates from reaching the reaction zone and actually acts as a "counter current" to back flush potential interfering particulates present in the original sample away from the reaction zone. The test analyte present in the fluid portion of the sample is bound to the complimentary immuno-reagent or chemical test reagent immobilized to the glass fiber matrix at the reaction zone site.

Subsequently, an immuno-reagent, or chemical test reagent in the case of a biochemical test, complimentary to the test analyte, conjugated with an enzyme or other suitable tracer, such as a radionuclide or fluorescent dye, is applied directly to the reaction zone. Unbound immuno-reagent conjugate or chemical test reagent is washed from the reaction zone in the lateral bi-directional mode outlined above by the application of a suitable wash volume applied directly to the reaction zone.

Sequentially, a suitable substrate or chromogen is added to the reaction zone. If the analyte was present in the sample, it will be sandwiched between the immobilized and enzyme conjugate immuno-reagents within the reaction zone. The enzyme conjugated to the analyte bound immuno-reagent acts upon the substrate or chromogen to produce a colored product within the reaction zone which may be viewed or measured with an instrument.

Exemplary Filter Construction and Methods of Utilizing Same

Example 1

Detection of Antibody to Rubella Virus in Whole Blood

Inactivated Rubella virus antigen is immobilized onto the reaction zone of the glass fiber matrix. This is followed by the addition of a blocking agent such as 1.0% bovine serum albumin or 0.5% non-fat milk suspension to the same area and allowed to dry.

The use of a blocking agent decreases the non-specific binding of extraneous proteins present in the fluid (serous) portion of whole blood to the reaction zone of the glass fiber matrix.

To perform an assay, approximately 30 microliters of whole blood is applied to the sample application zone of the device. This is followed by 60 microliters of a wash solution consisting of 0.5% non-fat milk in a phosphate buffered saline applied to the same area. Migration of the whole blood sample through the separation zone will filter and separate the cellular components from the sample within the area of the separation zone. Evidence of separation of the fluid portion of the whole blood sample is observed in the reaction zone by the appearance of serous fluids wetting the reaction zone area.

60 microliters of the wash solution is then applied to the wetted reaction zone. Upon absorption, the wash step is repeated. It will be noticed that the serous components and pigments contained therein will be eliminated via the lateral bi-directional mode described earlier from the reaction zone by this wash procedure.

However, if the whole blood specimen contains antibodies to the Rubella virus, the antibodies in the serous portion of the blood sample will bind to the Rubella virus antigens immobilized within the reaction zone of the glass fiber matrix. Then, 60 microliters of an affinity purified rabbit anti-human IgG alkaline phosphatase conjugate is applied to the reaction zone. This will bind to the antibody of the Rubella virus which may be present in the blood sample and will be trapped by the immobilized antigen located in the reaction zone of the glass fiber matrix. Unreacted enzyme conjugate is washed away as described above.

Finally, 60 microliters of a suitable substrate chromogen may be applied to the reaction zone. Appearance of a colored product at the reaction zone is evidence of enzyme activity and, therefore, indicative of antibody to Rubella virus present in the whole blood sample.

Example 2

Determination of Human Choriogonadotropin in Urine by a "Sandwich" Technique A polypeptide hormone, human choriogonadotropin (HCG), is secreted into the maternal circulatory system by the trophoblasts of the developing fetus. Ultimately, this hormone is excreted in the maternal urine. Detection of HCG in the urine is presumptive evidence of pregnancy. HCG is collected, concentrated and purified by well known published methods. The purified hormone may be used to generate antibodies (polyclonal or monoclonal) in the appropriate species, i.e., rabbits or mice, respectively.

The antibody of HCG is immobilized to the reaction zone of the glass fiber matrix. A blocking protein is then applied to the reaction zone as described in the previous example.

To determine if a urine specimen contains HCG, a few drops of the specimen are applied to the sample application zone of the glass fiber matrix of the device. This is followed by a sufficient volume of a wash solution applied to the same area to cause the sample to migrate through the separation zone toward and through the reaction zone of the glass fiber matrix which contains the immobilized antibody to HCG. If HCG is present in the sample, it will bind to the immobilized antibody located within the reaction zone.

Alternately, sufficient volume of urine may be applied to the sample application zone to cause the sample to chromatograph through the reaction zone without the use of a wash. In either case, migration of the urine sample through the separation zone will filter out urine particulates which may interfere in subsequent testing steps.

Then, a suitable volume of a washing solution is applied to the reaction zone. Lateral, bi-directional flow of the wash solution will carry unreacted urine components away from the reaction zone, i.e., away from the separation and sample application zones as well as toward the separation and sample application zones, reversing the original direction of flow. Movement toward the reaction zone of wash fluid in the latter direction prohibits further movement of unwanted particulates by counter flow forces. Indeed, subsequent addition of any wash or test reagent to the area of the reaction zone will force any trapped particulates or debris located within the separation zone away from the reaction zone.

Application to the reaction zone of an appropriate enzyme labeled antibody to HCG (either polyclonal or monoclonal) will bind to the HCG of the sample which has been trapped by the immobilized antibody bound to the reaction zone of the glass fiber matrix. Again, a wash solution is applied, as indicated above, to wash away, in a lateral, bi-directional mode, any unreacted enzyme conjugated antibody.

Subsequent addition of a suitable substrate chromogen solution to the reaction zone will indicate the presence of enzyme and, therefore, the presence of HCG, by the development of a colored product at the reaction zone. The method described above in this example is typical of a "sandwich technique", whereby the analyte, HCG in this case, is sandwiched between two antibodies, one immobilized to the glass fiber matrix of the reaction zone, the other conjugated to an enzyme or other suitable label. The presence of the HCG analyte is indicated by the development of color within the reaction zone.

Example 3

Determination of Human Choriogonadotropin in Urine by Competitive Inhibition Immunoassay The test devices of the invention are not limited to "sandwich" methodology, but may be applied to competitive inhibition techniques as described by the following example. Antibody immobilization, sample application and washing methods and separation/chromatographic principles are as described in the previous example. However, instead of application of an antibody enzyme conjugate, one may apply to the reaction zone an enzyme conjugate of the analyte, i.e., HCG coupled to an appropriate enzyme.

If HCG is present in the sample, it will bind to a finite and limited number of available antibody binding sites located and immobilized within the reaction zone of the glass fiber matrix. If the sample contains substantial amounts of HCG, then all available antibody binding sites in the reaction zone will be saturated.

Upon subsequent application of an enzyme conjugated to HCG (instead of enzyme conjugated to an anti-HCG antibody), all available immobilized antibody binding sites are saturated with the HCG from the sample and will not bind to the enzyme-HCG conjugate. When a suitable wash solution is applied, the enzyme-HCG conjugate will be washed away from the reaction zone in a lateral, bi-directional fashion.

Application of a suitable substrate chromogen solution to the reaction zone will not develop a color in this instance since no enzyme is available. If, however, the sample contains no or insufficient quantities of HCG to saturate all immobilized antibody binding sites, then HCG enzyme conjugate will bind to the available immobilized HCG binding sites and will not be washed away with subsequent washing steps.

Therefore, in this instance, upon subsequent application of a suitable substrate chromogen solution to the reaction zone of the glass fiber matrix, some color will develop, indicating the sample had little or no HCG present. In a competitive inhibition assay as just described, the absence of color development in the reaction zone is indicative of the presence of the analyte (HCG) in the sample, while the presence of color development in the reaction zone indicates little or no analyte (HCG) in the sample. The device can also be used for competitive immuno-assays of low molecular weight analytes, such as thyroid hormones, therapeutic drugs, steroids and other low molecular weight analytes.

Example 4

Detection of Glucose in Whole Blood

The device may be used to perform assays to indicate the presence or quantitation of analytes without employing immunological methods and principles. For example, one may detect the presence of glucose in whole blood by standard enzyme analytical techniques. In this instance, a mixture of the enzymes glucose oxidase and horseradish peroxidase is immobilized to the reaction zone of the device. Whole blood is then applied to the sample application zone.

A suitable wash solution is then applied to the sample application zone to effect the bi-directional lateral chromatographic separation of the fluid portion of the sample from the cellular components as described previously to introduce the fluid portion containing glucose into the reaction zone. The immobilized oxidase acts upon the glucose of the sample to produce D-glucono-δ-lactone and hydrogen peroxide.

The horseradish peroxidase, also immobilized within the reaction zone, catalyses the hydrogen peroxide in situ as it is generated. Subsequent addition to the reaction zone of a suitable chromogen test reagent will react with the products of catalysis to produce a colored product, the intensity of which is proportional to the amount of glucose present in the original sample. The intensity of color development may be observed visually or detected by the use of suitable instrumentation. It is evident from this example that the device of the invention accomplishes other than immunoassays with equal effectiveness.

It will be readily apparent that the utilization of the test devices manufactured in accordance with the teachings of this invention provides both more effective and less time-consuming testing of various suspensions in the field by relatively inexperienced personnel. The bilateral migration of the fluid components of the various samples applied to the application zones attributable to the unique construction of the test devices prevents the contamination of the reaction zones by the particulates in the suspension samples and also facilitates the migration of the fluid component of the sample to the reaction zones.

It is also contemplated by the invention that a plurality of test devices manufactured in accordance with the teachings of the invention and incorporating single application, separation and reaction zones may be snapped together or otherwise associated on a mounting board or the like to permit a series of different tests to be accomplished by juxtaposition of the single test devices.

It will be obvious to those skilled in the art that various modifications of the test devices of the invention may be made without departing from the scope of the claims.

We claim:

1. In a test device for performing solid phase immunoassays of a test sample having a liquid component, the combination of:
   a planar fiber filter matrix which absorbs and conducts fluid, said matrix including a test sample application zone, a separation zone and a reaction zone, said separation zone separating said application zone from said reaction zone and being sufficiently long to inhibit migration of particulates in said sample into said reaction zone; first absorbent material in communication with said sample application zone; and second absorbent material in communication with said reaction zone so as to cause bilateral flow of the liquid component of said test sample; said filter matrix at the location of communication between said sample application zone and said first absorbent material being constricted for causing said bilateral flow to be primarily from said application zone to said reaction zone, and secondarily from said application zone to said first absorbent material.

2. The device of claim 1 wherein said first absorbent material underlies said filter matrix.

3. The device of claim 1 in which said matrix is fabricated from a first material of a first porosity and said first and second absorbent materials are fabricated from a material of substantially different porosity from that of said first material.

4. The device of claim 1 in which said matrix has a range of pore sizes which prevent substantial migration of particulates in said sample from said absorption zone and said separation zone into said reaction zone, but permit bilateral flow of the liquid component of said test sample and any reagents accompanying the same into said reaction zone and permits bilateral flow of said fluid component and added reagents into said first and second absorbent materials.

5. The device of claim 4 in which said application zone is of bulbous configuration and said separation zone is constituted by an elongated shank portion integral with said application zone and with said reaction zone to permit fluid flow from said application zone through said separation zone into said reaction zone.

6. The device of claim 5, further including an extremity of said filter matrix overlying said first absorbent material so as to facilitate the aforesaid bilateral flow of said fluid component of said test sample.

7. In a test device for performing solid phase immunoassays, the combination of: a housing including a cover; first and second apertures through said cover; a planar filter matrix located in said housing under said cover, said filter matrix incorporating a test sample application zone at said first aperture, a separation zone in communication with said test sample application zone and a reaction zone at said second aperture in communication with said separation zone; first absorbent material located in said housing in fluid communication with said application zone; and second absorbent material in said housing in spaced relationship with said first absorbent material and in fluid communication with said reaction zone so as to cause bilateral flow of the fluid component of said test sample; said first aperture and said application zone being disposed between said first absorbent material and said reaction zone; and said second aperture and said reaction zone being disposed between said application zone and said second absorbent material.

8. The test device of claim 7 in which the fluid communication of said application zone with said first absorbent means is defined by said first absorbent means being disposed contiguous to a portion of the perimeter of said application zone.

9. The device of claim 7 in which said fluid communication between said first absorbent material and said application zone is defined by said first absorbent material being disposed below a portion of said filter matrix.

10. A method of performing an immunoassay in conjunction with a chromatographic test device which incorporates a planar filter matrix having sample application separation and reaction zones and first and second absorbent means in fluid communication respectively with said application and reaction zones so as to cause bilateral flow of fluids applied to said zones, comprising the steps of:
   applying a suitaBle volume of liquid sample containing particulates to said sample application zone;
   applying a suitable volume of wash reagent to said sample application zone;
   where after each of said sample and wash applications capillary forces within said filter matrix bilaterally draw the fluid portion of said sample primarily in the direction of said separation zone, but secondarily in the direction of said first absorbent means;
   and where said application and separation zones entrap said particulates;
   and where the fluid portion of said sample is drawn into said reaction zone which is treated with a reagent which reacts and binds with ananlyte component being assayed in said sample, said reagent being immobilized to the fiber matrix.
   applying a suitable volume of wash reagent to said reaction zone to wash away unreacted sample components under said bilateral flow away from the reaction zone and toward the separation and sample application zones;
   applying a tracer reagent complementary to said analyte component being assayed to said reaction zone, said tracer reagent being a reagent conjugated with a tracer;
   washing said reaction zone; and applying chromatic eliciting substrate to said reaction zone to produce a chromatic reaction determining the presence of said tracer in said reaction zone.

11. The method of claim 10 in which said tracer is an enzyme.

12. The method of claim 10 in which said tracer is a radionuclide.

13. The method of claim 10 in which said tracer is a fluorescent dye.

14. In a test device for performing solid phase immunoassays, the combination of:
a planar fiber filter matrix, said matrix including a test sample application zone, a separation zone and a reaction zone, said separation zone separating said application zone from said reaction zone and being sufficiently long to inhibit migration of particulates in said sample into said reaction zone; first absorbent material in communication with said sample application zone, and second absorbent material in communication with said reaction zone so as to cause bilateral flow of the liquid component of said test sample; said application zone being of bulbous configuration and said separation zone being an elongated relatively narrow shank portion integral with said application zone and with said reaction zone to permit fluid flow from said application zone through said separation zone into said reaction zone.

15. In a test device for performing solid phase immunoassays, the combination of:
a planar fiber filter matrix, said matrix including a test sample application zone, a separation zone and a reaction zone, said separation zone separating said application zone from said reaction zone and being sufficiently long to inhibit migration of particulates in said sample into said reaction zone; first absorption means in communication with said sample application zone, and second absorption means in communication with said reaction zone so as to cause bilateral flow of the liquid component of said test sample; the structure of said filter matrix at the location of said communic causing the bilateral flow to be primarily in the direction from said application zone to said reaction zone and secondarily in the opposite direction; said first and second absorbent means being of substantially larger cross section than said separation zone.

16. A method of performing an assay for an analyte in a sample fluid comprising:
immobilizing a specific reagent complimentary to said analyte to a reaction zone of a fiber filter matrix, said fiber filter matrix also having a sample application and separation zones, and first and second absorbent means in fluid communication, respectively, with said application and reaction zones so as to cause bilateral flow of fluids applied to said sample application zone.
applying a volume of said sample fluid to said sample application zone.
where said fiber matrix draws the fluid portion of said sample primarily in the direction fo the separation zone, but secondarily in the opposite direction under said bilateral flow;
and where said fibermatrix draws some of said fluid portion of said sample into said reaction zone;
and also where any analytes contained within said fluid drawn into said reaction zone react and bind with said specific reagent;
washing said reaction zone of unreacted sample components;
applying a tracer reagent which binds to said analyte component being assayed to said reaction zone said tracer reagent being a reagent conjugated with a tracer;
washing said reaction zone of unbound tracer reagent; and
determining the presence of said analyte in said sample by the presence or absence of said tracer in said reaction zone.

17. The method of claim 16, additionally comprising applying a blocking agent in order to decrease nonspecific binding of extraneous components of said sample after the step of immobilizing said reagent onto said reaction zone.

18. The method of claim 16, wherein said sample is a bodily fluid from a mammal.

19. The method of claim 18, wherein said bodily fluid is selected from the group consisting of blood and urine.

20. The method of claim 16, wherein said immobilized reagent is an antibody specific to said analyte, wherein said tracer reagent is a tracer conjugated to an antibody specific to said analyte, and wherein the presence of said tracer upon the completion of the assay indicates the presence of said analyte in said sample.

21. The method of claim 16, wherein said immobilized reagent is an antibody specific to said analyte, wherein said tracer reagent is a tracer conjugated to a molecule having an antigenic site reactive with said antibody, and wherein the absence of said tracer upon the completion of the assay indicates the presence of said analyte in said sample.

22. The method of claim 16, wherein said immobilized reagent is an antigen specific to a first antibody, said first antibody to be detected in said sample fluid, wherein said tracer reagent is a tracer conjugated to a second antibody, said second antibody being specific to said first antibody, and wherein the presence of said tracer upon the completion of the assay indicates the presence of said first antibody in said sample.

23. The method of claim 16, wherein said immobilized reagent is an antigen specific to a first antibody, said first antibody to be detected in said sample fluid, wherein said tracer reagent is a tracer conjugated to a second antibody, said second antibody being specific to said antigen, and wherein the absence of said tracer upon the completion of the assay indicates the presence of said first antibody in said sample.

24. A method of performing an immunoassay in conjuncation with a chromatographic test device which incorporates a planar filter matrix having sample application separation and reactionzones, and first and second absorbent means in fluid communication, respectively, with said with said application and reaction zones so as to cause bilateral flow of fluids applied to said zones, comprising the steps of:
applying a suitable volume of said sample fluid to said sample application zone;
where capillary forces within said fiber matrix draw the fluid portion of said sample primarily in the direction of said separation zone, but secondarily in the direction of said first absorbent means under said bilateral flow;
and where said application and separation zones entrap said particulates;
and also where the fluid portion of said sample is drawn into said reaction zone which is treated with a reagent which reacts and hinds with analyte component being assayed in said sample said reagent being immobilized to the fiber matrix;

washing said reaction zone to wash away unreacted sample components away from the reaction zone;

applying a tracer reagent complementary to said analyze component being assayed to said reaction zone, said tracer reagent being a reagent conjugated with a tracer;

washing said reaction zone, and determining the presence of said tracer in said reaction zone.

25. The method of claim 24, wherein the step of determining the presence of said tracer comprises applying chromic-eliciting substrate to said reaction zone, said substrate being acted upon by said tracer to produce a chromatic reaction.

26. The method of claim 24, additionally comprising applying a suitable volume of wash reagent to said sample application zone after the step of applying a suitable volume of liquid sample to said sample application zone.

27. The device of claim 1 in which such filter matrix includes a plurality of arms disposed in spaced relationship with one another, each of said arms including said test sample application zone, said separation zone and said reaction zone; each of said arms being in communication with said first and second absorbent

* * * * *